United States Patent
Hubers et al.

(10) Patent No.: US 10,406,159 B2
(45) Date of Patent: Sep. 10, 2019

(54) STABLE 5-METHYLTETRAHYDROFOLATE FORMULATIONS TO MODERATE METHYLENETETRAHYDROFOLATE REDUCTASE ASSOCIATED POLYMORPHISMS

(71) Applicant: La Vita Compounding Pharmacy, San Diego, CA (US)

(72) Inventors: Debra K. Hubers, Solana Beach, CA (US); Christine A. Givant, Solana Beach, CA (US)

(73) Assignee: La Vita Compounding Pharmacy, San Diego, CA (US)

( * ) Notice: Subject to any disclaimer, the term of this patent is extended or adjusted under 35 U.S.C. 154(b) by 0 days.

(21) Appl. No.: 15/546,650

(22) PCT Filed: Jan. 26, 2016

(86) PCT No.: PCT/US2016/014868
§ 371 (c)(1),
(2) Date: Jul. 26, 2017

(87) PCT Pub. No.: WO2016/123076
PCT Pub. Date: Aug. 4, 2016

(65) Prior Publication Data
US 2018/0000823 A1  Jan. 4, 2018

Related U.S. Application Data

(60) Provisional application No. 62/223,053, filed on Sep. 25, 2015, provisional application No. 62/108,474, filed on Jan. 27, 2015.

(51) Int. Cl.
| | | |
|---|---|---|
| A61K 31/519 | (2006.01) | |
| A61K 9/00 | (2006.01) | |
| A61K 9/08 | (2006.01) | |
| A61K 31/714 | (2006.01) | |
| A61K 47/02 | (2006.01) | |
| A61K 47/10 | (2017.01) | |
| A61K 47/12 | (2006.01) | |
| A61K 47/18 | (2017.01) | |
| A61K 47/20 | (2006.01) | |
| A61K 47/22 | (2006.01) | |
| C07D 475/04 | (2006.01) | |

(52) U.S. Cl.
CPC ............ *A61K 31/519* (2013.01); *A61K 9/006* (2013.01); *A61K 9/0019* (2013.01); *A61K 9/0043* (2013.01); *A61K 9/08* (2013.01); *A61K 31/714* (2013.01); *A61K 47/02* (2013.01); *A61K 47/10* (2013.01); *A61K 47/12* (2013.01); *A61K 47/183* (2013.01); *A61K 47/20* (2013.01); *A61K 47/22* (2013.01); *C07D 475/04* (2013.01)

(58) Field of Classification Search
CPC ........ A61K 47/22; A61K 47/10; A61K 47/12; A61K 47/183; A61K 47/20; A61K 47/02; A61K 31/519; A61K 31/714; A61K 9/0019; A61K 9/0043; A61K 9/006; A61K 9/08
See application file for complete search history.

(56) References Cited

U.S. PATENT DOCUMENTS

| | | | |
|---|---|---|---|
| 8,314,102 | B2 | 11/2012 | Manzotti |
| 2010/0168117 | A1 | 7/2010 | Manzotti |

FOREIGN PATENT DOCUMENTS

| | | | | |
|---|---|---|---|---|
| BR | PI0704182-9 A2 | 5/2009 | | |
| EP | 416 232 B1 | 8/1995 | | |
| EP | 2799061 A1 | * 11/2014 | ........... | A61K 31/519 |
| WO | WO 2014/146975 A1 | 9/2014 | | |

OTHER PUBLICATIONS

Definition of refrigeration, Oxford English Dictionary, http://www.oed.com/, accessed online on Aug. 30, 2018. (Year: 2018).*
Opladen et al., "Analysis of 5-Methyltetrahydrofotate in Serum of Healthy Children," *Mol. Gen. Metab.* (2006), 87:61-65, Elsevier Inc.
Seeking Health Active B12 Lozenge, (Nov. 8, 2014).

* cited by examiner

*Primary Examiner* — Jonathan S Lau
(74) *Attorney, Agent, or Firm* — DLA Piper LLP (US)

(57) ABSTRACT

Provided herein are methods for preparing stable solutions containing 5-methyltetrahydrofolate (MTHF). Also provided herein are stable compositions containing calcium 5-methyltetrahydrofolate (MTHF-Ca).

21 Claims, 3 Drawing Sheets

STABLE 5-METHYLTETRAHYDROFOLATE FORMULATIONS TO MODERATE METHYLENETETRAHYDROFOLATE REDUCTASE ASSOCIATED POLYMORPHISMS

CROSS-REFERENCE TO RELATED APPLICATIONS

This application is a 35 U.S.C. § 371 National Stage application of International Application No. PCT/US2016/014868 filed Jan. 26, 2016; which claims the benefit under 35 U.S.C. § 119(e) to U.S. Application Ser. No. 62/233,053 filed Sep. 25, 2015 and to U.S. Application Ser. No. 62/108,474 filed Jan. 27, 2015, both now expired. The disclosure of each of the prior applications is considered part of and is incorporated by reference in the disclosure of this application.

BACKGROUND OF THE INVENTION

Field of the Invention

The invention relates generally to a method for mitigating methylenetetrahydrofolate reductase (MTHFR) associated polymorphisms and specifically to stable formulations of the active form of folic acid, 5-methyltetrahydrofolate (MTHF).

Background Information

This invention relates to a method for mitigating methylenetetrahydrofolate reductase ("MTHFR") associated polymorphisms. MTHFR is an enzyme responsible for converting 5,10-methylenetetrahydrofolate to the active end product of folic acid, 5-methyltetrahydrofolate. Particularly, this invention relates to addressing MTHFR deficiency and its relation to chronic degenerative disease. Delivery of 5-methyltetrahydrofolate (MTHF), via a more direct route of delivery than is currently available is addressed.

Folic acid is commonly found in green leafy vegetables, legumes, nuts, orange juice and some fruits. Folic acid is a water-soluble form of vitamin B9 that the body requires for cell growth and reproduction.

Figure 1:
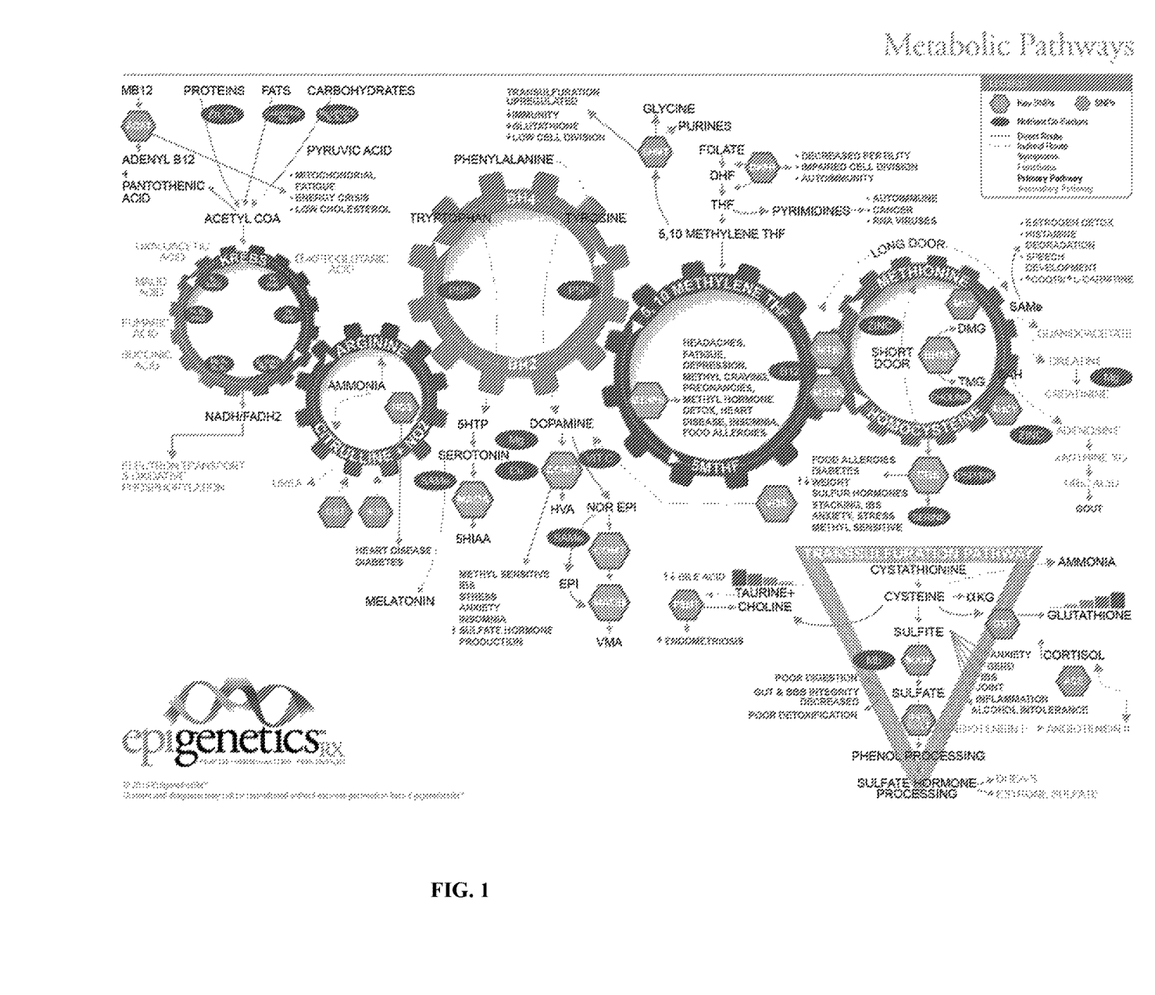
FIG. 1 illustrates the metabolic pathways associated with folic acid.
Figure 2:
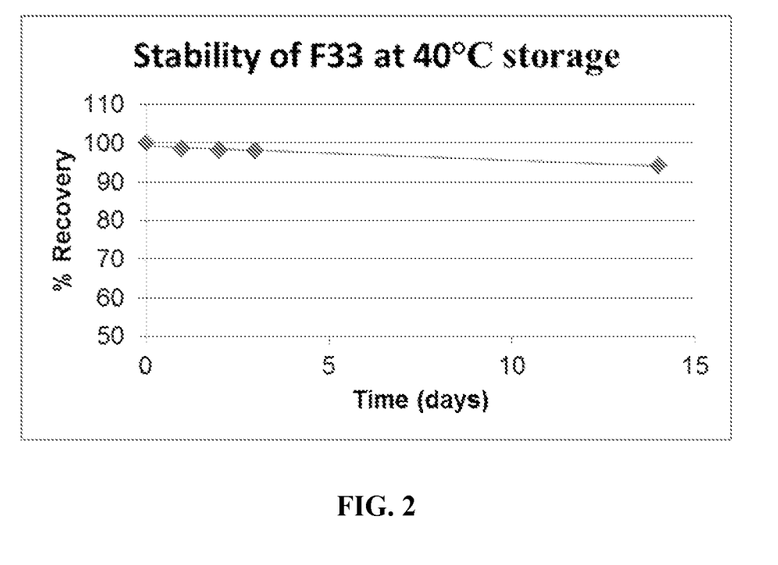
FIG. 2 shows the stability profile of 5-MTHF-Ca at 40° C.
Figure 3:
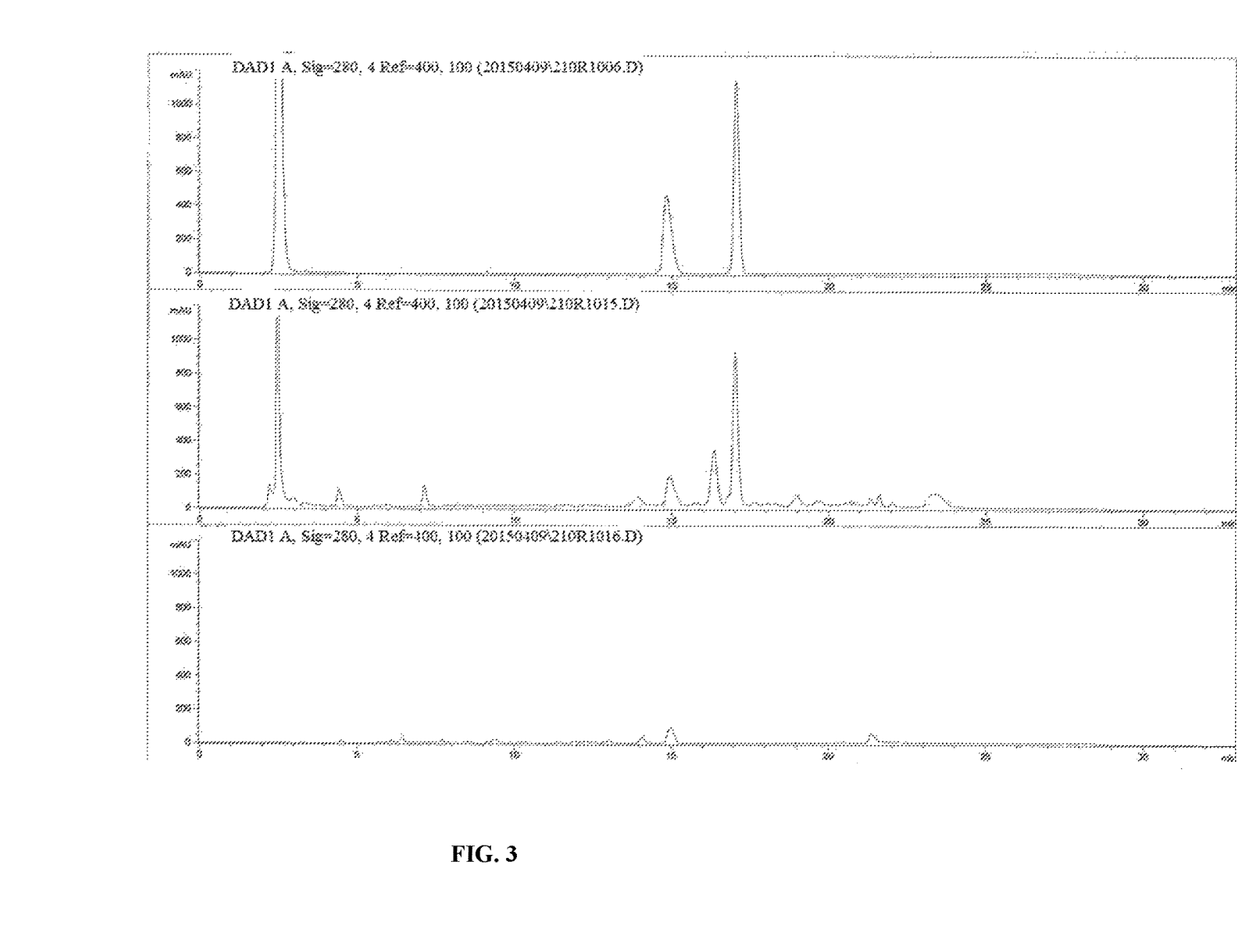
FIG. 3 discloses chromatograms of F42, Methyl Mate B and Methyl Factors (top to bottom). Note: HPLC assay of 5-MTHF in Methyl Mate B is 1.02 mg/mL. The concentration in the bottle is approximately 2 mg/mL, because the sample was diluted 2 fold for HPLC injection.

When digesting folic acid the body goes through several steps in order to "break down" the folic acid to its active form, 5-methyltetrahydrofolate, so it can be used properly. This is a complex process which is shown, step-by-step, in FIG. 1. As a result of these steps, the body makes a version of folic acid called MTHF.

Methyl groups are utilized extensively in the body for transport of nutrients in fat soluble states and in epigenetic processes, turning genes on or off. In patients with decreased activity in the methylation pathway, there is a shortage of methyl groups in the body required to execute a variety of important functions. Additionally, defects in methylation lay the appropriate groundwork for the further assault of environmental and infectious agents resulting in a wide range of conditions including diabetes, cardiovascular disease, thyroid dysfunction, neurological inflammation, diabetes, chronic viral infection, neurotransmitter imbalances, atherosclerosis, cancer, aging, schizophrenia, decreased repair of tissue damage, improper immune function, neural tube defects, Down's syndrome, Multiple Sclerosis, ADHD, Huntington's disease, Parkinson's disease, Alzheimer's and autism. Appropriate supplementation with vitamins and nutrients bypasses these mutations to allow for restored function of the pathway.

Not every individual with mutations in the methylation pathway will have one of the health conditions listed above. While may be a necessary element, there may not be a sufficient environmental or infectious trigger. Most health conditions in society today are multifactorial in nature. In essence, there is an underlying genetically determined risk that requires a significant infectious or environmental trigger to initiate the process. A certain threshold or body burden needs to be met for each of these factors in order for multifactorial disease to occur. However, part of what makes the methylation cycle so unique and so critical for health, is that mutations in this pathway have the capability to impair all three of these factors. This suggests that if an individual has sufficient mutations or weaknesses in their methylation pathway, this may be sufficient to cause the multifactorial disease by itself, as methylation cycle mutations can lead to chronic infectious diseases, increased environmental toxin burdens and have secondary effects on genetic expression.

According to a national testing laboratory, it is estimated that up to 45% of the United States population may have a mutation in at least one gene. Additionally, it has been reported that 70% of an identified depressed population has a MTHFR mutation. Conventional treatment for MTHF deficiency includes oral intervention with the vitamins folic acid and cyanocobalamin, which are inactive forms of these entities. The body must then convert both folic acid and cyanocobalamin to the active forms before it is able to utilize them. If one has a methylation mutation, they lack the ability to achieve this critical conversion. Studies illustrate that if an individual has compromised gut health, absorption of these vitamins may be greatly reduced. Therefore, there is a demand for a new stable route of delivery and new stable formulations that circumvent potential problems associated with oral absorption and/or inability to convert due to mutation.

SUMMARY OF THE INVENTION

The present invention is based on the seminal discovery of stable formulations of methyltetrahydrofolate calcium (MTHF-Ca) that allow for more effective routes of administration. Provided herein are methods for the preparation of stable 5-methyltetrahydrofolate (MTHF) solutions retaining a potency of from about 90% to 110% for up to 40 days when stored under refrigeration. The methods include: determining the weight of 5-methyltetrahydrofolate powder and sodium metabisulfite; determining the water content of the 5-methyltetrahydrofolate; adding an excess of between about 5% and 25% of 5-methyltetrahydrofolate powder; adding approximately 75% of the total desired volume of sterile water and mixing while keeping the mixture cold; mixing an appropriate amount of preservative into the mixture while keeping the mixture cold; adding a suitable gentle pH adjuster to adjust the pH to between approximately 3 and 9 while keeping the mixture cold; and adding enough sterile water to bring the mixture to the desired volume while protecting the mixture from light and keeping the mixture cold, where 5-methyltetrahydrofolate or a mixture containing 5-methyltetrahydrofolate is protected from light.

In certain embodiments, the excess of 5-methyltetrahydrofolate powder is about 15%. In other embodiments, the preservative comprises benzyl alcohol. In yet other embodiments, the method further includes adding a suitable gentle pH adjuster to adjust the pH to between approximately 4 and 8. In further embodiments, the gentle pH adjuster comprises sodium phosphate dibasic solution between about 1%-20%.

Also provided herein are compositions including: (i) about 0.5 to 1.5 mg/mL of calcium L-5-methyltetrahydrofolate (L-5-MTHF Ca); (ii) about 11-15 mg/mL citric acid monohydrate; (iii) about 1 to 30 mg/mL ascorbic acid; (iv) about 0.1 to 10 mg/mL edetate disodium dehydrate; (v) about 1 to 30 mg/mL monothioglycerol; (vi) metacresol; and (vii) NaOH or HCl to adjust to pH of about 5 to 8. In certain aspects, the compositions provided herein further include argon gas.

In certain aspects, the composition contains about 1 mg/mL of calcium 5-methyltetrahydrofolate (L-5-MTHF Ca). In other aspects, the composition contains about 12 mg/mL of citric acid monohydrate. In yet other aspects, the composition contains about 10 mg/mL ascorbic acid. In further aspects, the composition contains about 0.1 mg/mL edetate disodium dehydrate. In some aspects, the composition contains about 10 mg/mL monothioglycerol.

In certain aspects, the composition has a pH between about 3 to 9. In other aspects, the composition has a pH of between about 3.5 to 7. In yet other aspects, the composition is formulated as a solution. In one embodiment, the composition has a pH of between about 6 and 7, for example, the composition may have a pH of about 6.5. In another embodiment, the composition is formulated for injection by intravenous, intramuscular or subcutaneous administration. In another embodiment, the composition is formulated for sublingual administration. In yet another embodiment, the composition is formulated for intranasal administration and may be in the form of a spray. In further embodiments, the composition is formulated as a lozenge. In some aspects, the composition contains an additional therapeutic agent, including, but not limited to, a vitamin or mineral.

The claimed compositions/formulations can be lyophilized components and/or components from which water has been removed. These components are the components recited in the claimed compositions. Upon reconstitution to the desired volume and acid/base adjustment, compositions with the claimed concentrations and pH are obtained.

DETAILED DESCRIPTION OF THE INVENTION

The following terms, definitions and abbreviations apply. Abbreviations used herein have their conventional meaning within the chemical and biological arts.

The term "patient" refers to organisms to be treated by the methods of the disclosure. Such organisms include, but are not limited to, humans. In the context of the disclosure, the term "subject" generally refers to an individual who will receive or who has received treatment described below (e.g., administration of the compounds of the disclosure, and optionally one or more additional therapeutic agents).

The disclosure also provides pharmaceutical compositions comprising at least one compound in an amount effective for treating a disorder, and a pharmaceutically acceptable vehicle or diluent. The compositions of the disclosure may contain other therapeutic agents as described below, and may be formulated, for example, by employing conventional solid or liquid vehicles or diluents, as well as pharmaceutical additives of a type appropriate to the mode of desired administration (for example, excipients, binders, preservatives, stabilizers, flavors, etc.) according to techniques such as those well known in the art of pharmaceutical formulation.

The compounds of the disclosure may be formulated into therapeutic compositions as natural or salt forms. Pharmaceutically acceptable non-toxic salts include the base addition salts (formed with free carboxyl or other anionic groups), which may be derived from inorganic bases such as, for example, sodium, potassium, ammonium, calcium, or ferric hydroxides, and such organic bases as isopropylamine, trimethylamine, 2-ethylamino-ethanol, histidine, procaine, and the like. Such salts may also be formed as acid addition salts with any free cationic groups and will generally be formed with inorganic acids such as, for example, hydrochloric, sulfuric, or phosphoric acids, or organic acids such as acetic, citric, p-toluenesulfonic, methanesulfonic acid, oxalic, tartaric, mandelic, and the like. Salts of the disclosure include amine salts formed by the protonation of an amino group with inorganic acids such as hydrochloric acid, hydrobromic acid, hydroiodic acid, sulfuric acid, phosphoric acid, and the like. Salts of the disclosure may also include amine salts formed by the protonation of an amino group with suitable organic acids, such as p-toluenesulfonic acid, acetic acid, and the like. Additional excipients which are contemplated for use in the practice of the disclosure are those available to those of ordinary skill in the art, for example, those found in the United States Pharmacopeia Vol. XXII and National Formulary Vol. XVII, U.S. Pharmacopeia Convention, Inc., Rockville, Md. (1989), the relevant contents of which is incorporated herein by reference. In addition, polymorphs, hydrates, and solvates of the compounds are included in the disclosure.

The disclosed pharmaceutical compositions may be administered by any suitable means, for example, orally, sublingually; buccally; parenterally, such as by subcutaneous, intravenous, intramuscular, intrathecal, or intracisternal injection or infusion techniques (e.g., as sterile injectable aqueous or non-aqueous solutions or suspensions); nasally such as by inhalation spray; topically, such as in the form of a cream or ointment; or rectally such as in the form of suppositories; in dosage unit formulations containing non-toxic, pharmaceutically acceptable vehicles or diluents. The present compounds may, for example, be administered in a form suitable for immediate release or extended release. Immediate release or extended release may be achieved by the use of suitable pharmaceutical compositions comprising the present compounds, or, particularly in the case of extended release, by the use of devices such as subcutaneous implants or osmotic pumps. The present compounds may also be administered liposomally.

For buccal or sublingual administration, the compositions may take the form of tablets, lozenges, pastilles, or gels formulated in conventional manner. Such compositions may comprise the active ingredient in a flavored basis such as sucrose and acacia or tragacanth.

The term "therapeutically effective amount" means the amount of the compound or pharmaceutical composition that will elicit the biological or medical response of a tissue, system, animal or human that is being sought by the researcher, veterinarian, medical doctor or other clinician.

By "pharmaceutically acceptable" it is meant the carrier, diluent or excipient must be compatible with the other ingredients of the formulation and not deleterious to the recipient thereof.

The terms "administration of" and or "administering a" compound should be understood to mean providing a compound of the disclosure or pharmaceutical composition to the subject in need of treatment.

The pharmaceutical compositions for the administration of the compounds of this embodiment either alone or in combination with other agents, e.g., chemotherapeutic, may conveniently be presented in dosage unit form and may be prepared by any of the methods well known in the art of pharmacy. All methods include the step of bringing the active ingredient into association with the carrier which constitutes one or more accessory ingredients. In general, the pharmaceutical compositions are prepared by uniformly and intimately bringing the active ingredient into association with a liquid carrier or a finely divided solid carrier or both, and then, if necessary, shaping the product into the desired formulation. In the pharmaceutical composition the active object compound is included in an amount sufficient to produce the desired effect upon the process or condition of diseases. The pharmaceutical compositions containing the active ingredient may be in a form suitable for oral use, for aqueous or oily suspensions or solutions, syrups or elixirs.

Compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations.

Formulations for topical administration in the mouth, for example buccally or sublingually, include lozenges comprising the active ingredient in a flavored basis such as sucrose and acacia or tragacanth, and pastilles comprising the active ingredient in a basis such as gelatin and glycerin or sucrose and acacia.

Aqueous suspensions contain the active materials in admixture with excipients suitable for the manufacture of aqueous suspensions. Such excipients are suspending agents, for example sodium carboxymethylcellulose, methylcellulose, hydroxy-propylmethylcellulose, sodium alginate, polyvinyl-pyrrolidone, gum tragacanth and gum acacia; dispersing or wetting agents may be a naturally-occurring phosphatide, for example lecithin, or condensation products of an alkylene oxide with fatty acids, for example polyoxyethylene stearate, or condensation products of ethylene oxide with long chain aliphatic alcohols, for example heptadecaethylene-oxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. Also useful as a solubilizer is polyethylene glycol, for example. The aqueous suspensions may also contain one or more preservatives, for example ethyl, or n-propyl, p-hydroxybenzoate, one or more coloring agents, one or more flavoring agents, and one or more sweetening agents, such as sucrose or saccharin.

Oily suspensions may be formulated by suspending the active ingredient in a vegetable oil, for example *arachis* oil, olive oil, sesame oil or coconut oil, or in a mineral oil such as liquid paraffin. The oily suspensions may contain a thickening agent, for example beeswax, hard paraffin or cetyl alcohol. Sweetening agents such as those set forth above, and flavoring agents may be added to provide a palatable oral preparation. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present.

Syrups and elixirs may be formulated with sweetening agents, for example glycerol, propylene glycol, sorbitol or sucrose. Such formulations may also contain a demulcent, a preservative and flavoring and coloring agents.

The pharmaceutical compositions may be in the form of a sterile injectable aqueous or oleagenous suspension. This suspension may be formulated according to the known art using those suitable dispersing or wetting agents and suspending agents which have been mentioned above. The sterile injectable preparation may also be a sterile injectable solution or suspension in a parenterally-acceptable diluent or solvent or cosolvent or complexing agent or dispersing agent or excipient or combination thereof, for example 1,3-butane diol, polyethylene glycols, polypropylene glycols, ethanol or other alcohols, povidones, Tweens, sodium dodecyl sulfate, sodium deoxycholate, dimethylacetamide, polysorbates, poloxamers, cyclodextrins, e.g., sulfobutyl ether β-cyclodextrin, lipids, and excipients such as inorganic salts (e.g., sodium chloride), buffering agents (e.g., sodium citrate, sodium phosphate), and sugars (e.g., saccharose and dextrose). Among the acceptable vehicles and solvents that may be employed are water, dextrose solutions, Ringer's solutions and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

Depending on the condition being treated, these pharmaceutical compositions may be formulated and administered systemically or locally. Techniques for formulation and administration may be found in the latest edition of "Remington's Pharmaceutical Sciences" (Mack Publishing Co, Easton Pa.). Suitable routes may, for example, include oral or transmucosal administration; as well as parenteral delivery, including intramuscular, subcutaneous, intramedullary, intrathecal, intraventricular, intravenous, intraperitoneal, or intranasal administration. For injection, the pharmaceutical compositions of the disclosure may be formulated in aqueous solutions, for example, in physiologically compatible buffers such as Hanks' solution, Ringer's solution, or physiologically buffered saline. For tissue or cellular administration, penetrants appropriate to the particular barrier to be permeated are used in the formulation. Such penetrants are generally known in the art. Pharmaceutical formulations for parenteral administration include aqueous solutions of the active compounds in water-soluble form. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances that increase the viscosity of the suspension, such as sodium carboxymethyl cellulose, sorbitol, or dextran. Optionally, the suspension may also contain suitable stabilizers or agents that increase the solubility of the compounds to allow for the preparation of highly concentrated solutions.

In the methods described herein, an appropriate dosage level will generally be about 0.01 to 500 mg, which can be administered in single or multiple doses. The dosage level can be about 0.01 to about 250 mg, such as 0.01 to about 100 mg, for example, 0.01 to about 10 mg, such as about 1 to 5 mg, or about 0.5 to about 100 mg. A suitable dosage level may be also about 0.05 to 100 mg, or about 0.1 to 50 mg or 1.0 mg. Within this range the dosage may be 0.05 to 0.5, 0.5 to 5 or 5 to 50 mg for example. The compounds may be administered daily, weekly or monthly. For example, the compounds may be administered on a regimen of one time per day or one time per week. There may be a period of no administration followed by another regimen of administration. Administration of the compounds may be closely associated with the schedule of a second agent of administration.

It will be understood, however, that the specific dose level and frequency of dosage for any particular patient may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the host undergoing therapy.

There are many commercially available injectable vitamin solutions, all of which require a prescription due to the route of administration. The most common are B-Complex and Cyanocobalamin (Vitamin B12). Cyanocobalamin is a synthetic form of vitamin B12 that is used to prevent and treat low blood levels of this vitamin. Vitamin B12 is important to maintain the health of metabolism, blood cells and nerves. An injectable form may be prescribed when oral forms have shown little or no improvement due to gut issues. A practitioner might prescribe a vitamin B12 injection to treat a low number of red blood cells (anemia), permanent nerve damage intestinal/stomach problems, poor nutrition, cancer, HIV infection, pregnancy, old age and/or alcoholism.

The limitations with cyanocobalamin are similar to those with folic acid: the body has to convert it to the active form of methylcobalamin in order to be able to utilize it. A large portion of the population has a methylation mutation preventing them from converting to the active form by natural physiological processes. Additionally, patients with gut issues have problems with absorption. One way to bypass both of these issues is to use a methylcobalamin injection.

Currently there are no commercially available methylcobalamin injections on the market. Therefore, practitioners have turned to Compounding Pharmacies to formulate methylcobalamin injections for use on their patients. The clinical success of the methylcobalamin injections have led to practitioners to request an injectable form of active folic acid, 5-methyltetrahydrofolate, (MTHF) as well.

One or more of the following compounds can be included in the foregoing compositions/formulations: Methylcobalamin, Hydroxocobalamin, Adenosylcobalamin, Thiamine, Riboflavin-5-phosphate, Niacinamide, Pyridoxine, Dexpanthenol, Biopterin, Inositol, Choline, Methionine and Glutathione.

Previously MTHF had not been commercially available in a solution form. This is possibly attributable to the relative instability of MTHF. Attempts to formulate a solution utilizing standard methodologies used in formulating other common injectable vitamins were unsuccessful. Analytical testing showed that the end product potency dropped to 0% in three days. Research and development led to a very specific formulation process. Continual testing provided quantitative evidence guiding the research and development process resulting in a stable formulation. MTHF produced by the process disclosed herein retained a potency of more than 100% and as high as 109.8% for up to 40 days when stored under refrigeration.

Once the formulation was stabilized, the demand from practitioners grew for injectable MTHF as a direct result of the positive initial clinical outcomes observed by several dozen practitioners. Prescribers informally shared positive outcomes in the following areas: neuropathic pain, depression, migraines, down's syndrome, hormone imbalances, cardiovascular markers, diabetes/metabolic syndrome and cancer. One physician at a major hospital chain included the compounded MTHF injection in a formal depression study. Notably, one patient who tested at greater than level 30 on the Hamilton Depression Scale, which is considered suicidal, subsequently scored an 11 (with 8 being normal and happy), after 4 months of weekly injections of the MTHF formulations described herein. The patient had previously taken multiple combinations of various commercially available anti-depressants with no success.

Currently, a large accredited medical university is partnering with the neurological department of a large accredited hospital chain to conduct a formal case study review of the MTHF injection and formulations disclosed herein. The case study will focus on patients with a primary diagnosis of migraines and a secondary diagnosis of depression.

A stable formulation having the following target properties was developed:

A solution formulation with each milliliter containing 1 mg MTHF-Ca;

Contains benzyl alcohol as a preservative;

Has T90 at 2-8° C. and at 25° C. if possible (T90 is the duration in which 90% intact MTHF-Ca remains);

Contains suitable excipients to permit lyophilization;

Not containing any excipient known to cause hemolysis, local toxicity or hypersensitivity reactions;

Not containing sulfites;

Is at a neutral or near neutral pH (e.g., 5-7.5) or as close to a neutral pH as permitted by the solubility/stability of MTHF-Ca; and Is isotonic or as close to being isotonic as permitted by the solubility/stability of MTHF-Ca.

In order to prepare the stable formulations disclosed herein, a pH stability/rate profile was generated in accordance with the following testing protocol: (i) prepare a sufficient number of test solutions all at the same concentration of MTHF-Ca; (ii) vary the pH of the test solutions by preparing samples of 6-8 different pH solutions with all solutions falling within the pH range of 4-7; and (iii) vary the storage temperature of each of the different pH solutions by storing at least one of each pH solution at the following temperatures: 2-8° C., 25° C. and 40° C.

Each of the test solutions treated under the various conditions set forth above were analyzed for concentration of MTHF-Ca and total impurities at a minimum of two different appropriate time points using the HPLC Assay Method. The study is intended to determine (a) the pH region where MTHF-Ca is most stable (pHmax); (b) the degradation profile at pHmax; (c) retention time of the top six impurities at pHmax by HPLC retention time; and (d) the long-term stability prognosis of MTHF-Ca at pHmax.

Based on the pH-stability profile, a solution of MTHF-Ca was prepared at the pHmax and test sensitivity of MTHF-Ca to light exposure according to the ICH/FDA light stability testing conditions. The following features were determined: (a) if controlled room lighting is necessary during the preparation of a MTHF-Ca solution, and (b) if amber glass vials are necessary for a MTHF-Ca solution.

A real-time stability testing up to 60 days including 3 pulls was conducted. In each pull, the tests included pH, appearance, USP particulate matter, assay and impurity. T90 was and all major impurities were determined and all major impurities.

Particular MTHF and MTHF-Ca formulations and processes of preparing the formulations are described herein.

EXAMPLE 1

Process for the Preparation of an Inectable MTHF Solution

This example illustrates a process for preparing a stable MTHF formulation.

The formulation process disclosed herein addresses temperature, pH, oxygen and light sensitivity. Specific pH adjusters within the formulation proved more critical than the resulting pH. Regarding temperature, the Materials Safety Data Sheet (MSDS) accompanying the raw ingredient stated that the raw ingredient was not temperature sensitive. However, modifying the temperature directly affected the potency duration. A very specific and compatible anti-oxidant was incorporated to affect the formulation's tendency to reduce. Formulation processes related to light sensitivity resulted in the compound reducing rapidly and losing potency. Standard light sensitivity formulations procedures still did not produce a satisfactory duration of stability. Modifications to the procedures directly and indirectly affiliated with the sterile room equipment were performed and have a significant effect on the outcome of the MTHF formulation's stability. Specific procedures include weighing, filtering and filling processes.

The amount of MTHF weighed was adjusted to account for assay and water content of the raw ingredient of each specific lot. Formulation must take into account water content of assay. Furthermore, an additional amount of active ingredient above this was added to account for rapid degradation.

Compounding a 100 ml batch of MTHF injectable starts with weighing the exact amount of 5-methyltetrahydrofolate powder and an appropriate anti-oxidant such as sodium metabisulfite in a powder hood utilizing extreme caution to protect from close direct light. Calculations are first completed to account for the specific lot of MTHF's assay potency and water content. An additional amount of MTHF is then added to this to account for loss of stability due to oxidation. The additional amount is preferably between 5% and 25% and most preferably an additional approximately 15%. The powdered ingredients must be put into solution and must be protected from light and kept cool. One suitable method of mixing while protecting the mixture from light and keeping it cool is to wrap the beaker in foil and place on spin plate in an ice bath. Then add approximately 75% of the total volume of sterile water needed to make up the desired volume. Add a preservative while spinning, keeping the mixture cool and protecting it from light. One suitable preservative is benzyl alcohol 2%. Then add a pH adjuster drop by drop until the appropriate pH is achieved. One example of a suitable pH adjuster is sodium phosphate dibasic solution 1%-20%. The appropriate pH is preferably between approximately 3 and approximately 9, more preferably between approximately 4 and approximately 8 and most preferably between approximately 5 and approximately 5.7. Bring the solution to the desired volume with the remaining sterile water while utilizing extreme caution to protect from direct light and keeping the mixture cool. Filter through a 0.22 micron filter into sterile vials. The vials preferably protect the mixture from light such as amber or opaque vials. Refrigerate immediately after filtering and labeling.

EXAMPLE 2

Methylfolate Calcium Sublingual Drop 1 mg/ml

1. Take 100 mL WFI water in to a new sterile Nalgene bottle
2. Weigh ascorbic acid, citric acid, EDTA Disodium, Glutathione, glycerin, potassium sorbate and 5-L-MTHF-Ca.
3. Shake to dissolve and dilute by WFI to 40 g
4. Adjust pH to 6.5 using HCl/NaOH
5. QS WFI water to 50 g
6. Aseptically in a biosafety hood, fill in dropper bottles and cap it
7. Place upstanding position on stability chamber

| Composition | | | | |
|---|---|---|---|---|
| % wt | Grade, lot and source | F35 | F42 | F43 |
| 5-L-MTHF-Ca | USP, Attix pharmaceuticals, 120926 | 0.1 | 0.1 | 0.1 |
| Citric acid monohydrate | USP, Spectrum, WJ0374 | 1.26 | 1.26 | 1.26 |
| Ascorbic acid | USP, Spectrum, 1DJ0866 | 1 | 1 | 1 |
| EDTA disodium dehydrate (EDTA) | USP, J. T. Baker, H45593 | 0.01 | 0.01 | 0.01 |
| L-Glutathione reduced | Spectrum, 1CD0493 | 0.5 | 0.5 | 0.5 |
| Glycerin* | Synthetic, Dow | | 25 | 50 |
| Potassium sorbate** | Sigma-Aldrich | | 0.13 | 0.13 |
| pH | | 6.5 | 6.5 | 6.5 |

*To replace water for better stability
**Added as a preservative

| Compounding g/50 | F35 | F42 | F43 |
|---|---|---|---|
| 5-L-MTHF-Ca | 0.05 | 0.05 | 0.05 |
| Citric acid monohydrate | 0.63 | 0.63 | 0.63 |
| Ascorbic acid | 0.5 | 0.5 | 0.5 |
| EDTA | 0.01 | 0.01 | 0.01 |
| Glutathione | 0.25 | 0.25 | 0.25 |
| Glycerin | | 12.5 | 37.5 |
| Potassium sorbate | | 3.75 | 3.75 |
| pH | 6.5 | 6.5 | 6.5 |

Stability Results

| | | Appearance | | | | |
|---|---|---|---|---|---|---|
| ID | Temp (° C.) | T = 0 (Initial) | 1 month | 2 month | 3 month | 6 month |
| F35 | 2-8 | Clear, colorless liquid | No change | No change | No change | Yellow |

-continued

| | | Appearance | | | | |
|---|---|---|---|---|---|---|
| ID | Temp (° C.) | T = 0 (Initial) | 1 month | 2 month | 3 month | 6 month |
| | 25 | | No change | Yellow | Yellow | Yellow |
| | 40 | | No change | Yellow | Yellow | Yellow |
| F42 | 2-8 | Clear, colorless liquid | No change | No change | No change | Yellow |
| | 25 | | No change | No change | Yellow | Yellow |
| | 40 | | Yellow | Yellow | Yellow | Yellow |
| F43 | 2-8 | Clear, colorless liquid | No change | No change | No change | Slightly yellow |
| | 25 | | No change | No change | Yellow | Yellow |
| | 40 | | Yellow | Yellow | Yellow | Yellow |

| | | Assay (mg/mL) by HPLC | | | | |
|---|---|---|---|---|---|---|
| ID | Temp (° C.) | T = 0 (Initial) | 1 month | 2 month | 3 month | 6 month |
| F35 | 2-8 | 1.04 | 1.05 | 1.06 | 1.04 | 0.97 |
| | 25 | | 1.05 | 1.02 | 0.96 | ND |
| | 40 | | 1.05 | 1.06 | 1.01 | 0.76 |
| F42 | 2-8 | 1.07 | 1.07 | 1.08 | 1.08 | 1.06 |
| | 25 | | 1.07 | 1.08 | 1.07 | 0.96 |
| | 40 | | 1.07 | 1.02 | 0.86 | 0.38 |
| F43 | 2-8 | 1.15 | 1.15 | 1.16 | 1.17 | 1.16 |
| | 25 | | 1.15 | 1.16 | 1.15 | 1.06 |
| | 40 | | 1.14 | 1.09 | 0.88 | 0.28 |

| | | Assay recovery (over initial) | | | | |
|---|---|---|---|---|---|---|
| ID | Temp (° C.) | T = 0 (Initial) | 1 month | 2 month | 3 month | 6 month |
| F35 | 2-8 | 1.00 | 99 | 100 | 98 | 91 |
| | 25 | | 98 | 96 | 90 | ND |
| | 40 | | 99 | 99 | 95 | 71.4 |
| F42 | 2-8 | 1.00 | 100 | 101 | 101 | 99.2 |
| | 25 | | 100 | 101 | 99 | 89.4 |
| | 40 | | 100 | 95 | 80 | 35.0 |
| F43 | 2-8 | 1.00 | 100 | 101 | 102 | 101.2 |
| | 25 | | 100 | 101 | 100 | 92.6 |
| | 40 | | 99 | 95 | 77 | 24.1 |

| | | Total chromatographic purity (% Peak Area) | | | | |
|---|---|---|---|---|---|---|
| ID | Temp (° C.) | T = 0 (Initial) | 1 month | 2 month | 3 month | 6 month |
| F35 | 2-8 | 99.2 | 99.0 | 97.0 | 97.7 | 95.5 |
| | 25 | | 98.7 | 90.5 | 94.8 | ND |
| | 40 | | 99.0 | 81.8 | 78.7 | ND |
| F42 | 2-8 | 99.4 | 99.2 | 99.1 | 99.1 | 97.4 |
| | 25 | | 99.1 | 91.4 | 97.1 | ND |
| | 40 | | 98.3 | 78.3 | 72.3 | ND |
| F43 | 2-8 | 99.2 | 99.2 | 99.1 | 99.3 | 98.7 |
| | 25 | | 99.1 | 97.9 | 97.4 | 86.3 |
| | 40 | | 98.4 | 84.6 | 71.7 | ND |

| | | pH | | | | |
|---|---|---|---|---|---|---|
| ID | Temp (° C.) | T = 0 (Initial) | 1 month | 2 month | 3 month | 6 month |
| F35 | 2-8 | 6.68 | 6.50 | 6.44 | 6.60 | 6.34 |
| | 25 | | 6.35 | 6.37 | 6.46 | ND |
| | 40 | | 6.44 | 6.34 | 6.46 | ND |
| F42 | 2-8 | 6.48 | 6.38 | 6.28 | 6.46 | 6.40 |
| | 25 | | 6.58 | 6.19 | 6.36 | ND |
| | 40 | | 6.49 | 5.95 | 6.11 | ND |
| F43 | 2-8 | 6.44 | 6.36 | 6.47 | 6.50 | 6.45 |
| | 25 | | 6.53 | 6.41 | 6.42 | 6.39 |
| | 40 | | 6.52 | 6.23 | 6.26 | ND |

Conclusions

The 1 month stability data indicates:

F35 is stable without any significant change in appearance, pH, assay and impurity. It appears the best among the 3 formulations tested.

F35 may be also considered as a candidate for IM injection without need for inert gas, i.e., a backup for F41.

Headspace in the final package is important for stability. A low headspace-to-liquid ratio such as 1:15 or less is desired.

F42 and F43 turned yellow at 40° C. The color change is likely due to degradation of the antioxidant ascorbic acid.

The 2 month stability data indicates:

All the formulations remained stable at 2-8 and 25° C. storage.

F42 and F43 (containing Glycerin) showed better stability than F35 did at 2-8 and 25° C. storage.

The 3 month stability data suggests:

F35, F42 and F43 are stable at 2-8 and 25° C. storage. Samples stored at 2-8° C. remained clear and colorless, the ones stored at 25 and 40° C. turned yellow.

The 6 month stability data suggests:

F35, F42 and F43 are stable at 2-8° C. storage.

T90 of F43 is about 6 months at 25° C.

EXAMPLE 3

Objective
1. To prepare a large batch (0.6 L) of F40
2. To observe long-term stability at 2-8 and 25° C. and accelerated stability at 30 and 40° C.

Materials

| Materials needed | Source, grade and lot |
|---|---|
| 5-L-MTHF, USP | Attix pharmaceuticals, Lot#: 120926 |
| Sodium hydroxide, NF | Spectrum, Lot#: TH0424 |
| Citric acid (anhydrous), USP | Spectrum, Lot#: QR0464 |
| Ascorbic acid, USP | Spectrum, Lot#: TK1234 |
| EDTA disodium dihydrate, USP | J. T. Baker, Batch#: 0000048326 |
| Monothioglycerol | Spectrum, Lot# 2BJ0502 |
| Metacresol, USP | Spectrum, Lot# 1BF0883 |
| WFI | Omnipur, Lot# 98072042 |

Experiments

| Composition table | |
|---|---|
| Name | F40 (mg/mL) |
| 5-L-MTHF-Ca | 1 |
| Citric acid monohydrate | 12.6 |
| Ascorbic acid | 10 |

-continued

| Composition table | |
|---|---|
| Name | F40 (mg/mL) |
| EDTA disodium dihydrate | 0.1 |
| Monothioglycerol | 10 |
| Metacresol | 1 |
| Argon | + |
| pH | 6.5 |

Preparation Procedure
1. Transfer 1000 mL WFI into a new 1 L sterile Nalgene
2. Sonicate 30 min to de-gas
3. Into another new 1 L sterile Nalgene bottle
4. Weigh out and add ascorbic acid, citric acid, EDTA disodium dihydrate, monothioglycerol and metacresol
5. Add WFI to 500 mL and mix to dissolve all solids
6. Adjust pH to 6.5 using HCl/NaOH
7. Weigh out and add 5-L-MTHF-Ca
8. QS WFI to 660 g
9. Keep on ice and purge with 0.2 μm filtered argon for 10 minutes
10. In a biosafety hood Pass through a 0.2 μm vacuum filter (VWR bottle top filtration, 1000 mL, 0.2 μm PES, Lot#500013941)
11. Aseptically in a biosafety hood, manually fill 30 mL filtrate to each 30 mL sterile glass vial (Greer®, Lot#237728) using a 30 mL BD sterile syringe
12. Aseptically in a biosafety hood, fill the headspace with 0.2 μm filtered argon
13. Aseptically in a biosafety hood, seal with rubber stoppers (Greer®) and crimp the vials
14. Label each vial
15. Place upstanding position in 2-8, 25, 30 and 40° C. stability chambers Stability Results

| Appearance | | | | | |
|---|---|---|---|---|---|
| Temp (° C.) | T = 0 (Initial) | 2 weeks | 1 month | 2 month | 3 month |
| 2-8 | Clear, colorless liquid | Clear, colorless liquid | Clear, colorless liquid | Clear, colorless liquid | Clear, colorless liquid |
| 25 | Clear, colorless liquid | Clear, colorless liquid | Clear, colorless liquid | Clear, colorless liquid | Clear, colorless liquid |
| 30 | Clear, colorless liquid | Clear, colorless liquid | Clear, colorless liquid | Clear, colorless liquid | Clear, colorless liquid |
| 40 | Clear, colorless liquid | Clear, colorless liquid | Clear, colorless liquid | Clear, colorless liquid | Clear, colorless liquid |

| Assay (mg/mL) by HPLC | | | | | |
|---|---|---|---|---|---|
| Temp (° C.) | T = 0 (Initial) | 2 weeks | 1 month | 2 month | 3 month |
| 2-8 | 1.04 | ND | 1.03 | 1.02 | 1.00 |
| 25 | 1.04 | ND | 1.03 | 1.03 | 1.00 |
| 30 | 1.04 | 1.03 | 1.03 | 1.03 | 1.00 |
| 40 | 1.04 | 1.03 | 1.03 | 1.03 | 1.00 |

| Assay recovery (over initial) | | | | | |
|---|---|---|---|---|---|
| Temp (° C.) | T = 0 (Initial) | 2 weeks | 1 month | 2 month | 3 month |
| 2-8 | 1.00 | ND | 0.99 | 0.99 | 0.97 |
| 25 | 1.00 | ND | 0.99 | 0.99 | 0.97 |
| 30 | 1.00 | 0.99 | 0.99 | 0.99 | 0.97 |
| 40 | 1.00 | 0.99 | 0.99 | 0.99 | 0.97 |

| Total chromatographic purity (% Peak Area) | | | | | |
|---|---|---|---|---|---|
| Temp (° C.) | T = 0 (Initial) | 2 weeks | 1 month | 2 month | 3 month |
| 2-8 | 99.4 | ND | 99.3 | 99.2 | 99.4 |
| 25 | 99.4 | ND | 99.3 | 99.3 | 99.4 |
| 30 | 99.4 | 99.4 | 99.4 | 99.2 | 99.4 |
| 40 | 99.4 | 99.3 | 99.5 | 98.9 | 99.0 |

| Major impurity (% Peak Area) Mefox* | | | | | |
|---|---|---|---|---|---|
| Temp (° C.) | T = 0 (Initial) | 2 weeks | 1 month | 2 month | 3 month |
| 2-8 | 0.64 | ND | 0.68 | 0.62 | 0.64 |
| 25 | 0.64 | ND | 0.67 | 0.59 | 0.57 |
| 30 | 0.64 | 0.60 | 0.50 | 0.46 | 0.38 |
| 40 | 0.64 | 0.53 | 0.62 | 0.30 | 0.21 |

*Impurity with peak area exceeding 0.1%

F40 exhibited good stability after 3 month at 2-8, 25, 30 and 40° C.

EXAMPLE 4

Objective
To prepare a batch of F41 (F40 without inert gas)
To observe the stability stored at 40, 25 and 2-8° C.

| Composition | | |
|---|---|---|
| Mg/mL | Grade, lot and source | Mg/mL* |
| 5-L-MTHF-Ca | USP, Attix pharmaceuticals, Lot#: 120926 | 1 |
| Citric acid monohydrate | USP, Spectrum, WJ0374 | 12.6 |
| Ascorbic acid | USP, Spectrum, 1DJ0866 | 10 |
| EDTA sodium | USP, J. T. Baker, H45593 | 0.1 |
| Monothioglycerol | Spectrum, 2BJ0502 | 10 |
| Metacresol | USP, Spectrum, 1BF0883 | 1 |
| pH | | 6.5 |

RT density = _1.016_g/mL

| Compounding ( ) | |
|---|---|
| | Target (g/g) |
| 5-L-MTHF-Ca (g) | 0.05 |
| Citric acid monohydrate (g) | 0.63 |
| Ascorbic add (g) | 0.5 |
| EDTA sodium (g) | 0.01 |
| Monothioglycerol (g) | 0.5 |
| Metacresol (g) | 0.05 |
| pH | 6.5 |
| DI water qs (g) | 50 |

Preparation Procedure
1. Take 100 mL WFI water in to a new sterile Nagene bottle 2. Weigh ascorbic acid, citric acid, EDTA Disodium, monothioglycerol, metacresol and 5-L-MTHF-Ca.
3. Shake to dissolve and dilute by WFI to 40 g
4. Adjust pH to 6.5 using HCl/NaOH
5. QS WFI water to 50 g
6. Aseptically in a biosafety hood, fill 2 mL glass vials by passing thru a 0.2-micron syringe filter, seal the vials immediately
7. Label each vial
8. Place upstanding position on stability chamber Test
9. Record appearance
10. HPLC for assay and impurity
11. pH Stability Results

Appearance

| Temp (° C.) | T = 0 (Initial) | 1 month | 1.5 month |
|---|---|---|---|
| 2-8 | Clear, colorless | No change | No change |
| 25 | | | |
| 40 | | | |

Assay (mg/mL) by HPLC

| Temp (° C.) | T = 0 (Initial) | 1 month | 1.5 month |
|---|---|---|---|
| 2-8 | 1.04 | 0.97 | 1.05 |
| 25 | | 0.97 | 1.05 |
| 40 | | 0.97 | 1.04 |

Assay recovery (over initial)

| Temp (° C.) | T = 0 (Initial) | 1 month | 1.5 month |
|---|---|---|---|
| 2-8 | 1.00 | 0.94 | 1.01 |
| 25 | | 0.94 | 1.02 |
| 40 | | 0.94 | 1.01 |

Total chromatographic purity (% Peak Area)

| Temp (° C.) | T = 0 (Initial) | 1 month | 1.5 month |
|---|---|---|---|
| 2-8 | 99.2 | 99.1 | 99.1 |
| 25 | | 99.2 | 99.2 |
| 40 | | 99.0 | 99.1 |

Major impurity (% Peak Area) Mefox*

| Temp (° C.) | T = 0 (Initial) | 1 month | 1.5 month |
|---|---|---|---|
| 2-8 | 0.61 | 0.80 | 0.79 |
| 25 | | 0.68 | 0.67 |
| 40 | | 0.64 | 0.54 |

*Impurity that grows

F41 appears stable at 1.5 month stability pull.

EXAMPLE 5

Objective
To re-formulate MTHF-Ca with excipients available by client
To observe the stability stored at 25 and 40° C.

Composition (%)

| Mg/mL | Grade, lot and source | F44 | F46 | F47 |
|---|---|---|---|---|
| 5-L-MTHF-Ca | 120926, Attix pharmaceuticals | 1 | 1 | 1 |
| Citric acid anhydrous | USP, 1403190098 | | 11.5 | 11.5 |
| Ascorbic acid | USP, 125157/J, Medisca | 10 | 10 | 10 |
| EDTA sodium | EP, 120998/c | 0.1 | 0.1 | 0.1 |
| Glutathione | 122805/A | | | 5 |
| Benzyl alcohol | NF, RM15-0198/A | 10 | 10 | 10 |
| pH | | 6.5 | 6.5 | 6.5 |
| WFI | USP, 986720710mnipur | QS | QS | QS |

Density at room temperature = 1.016 g/mL

Compounding (30 mL batch)

| | F44 (g/30 mL) | F46 (g/30 mL) | F47 (g/30 mL) |
|---|---|---|---|
| 5-L-MTHF-Ca* | 0.035 | 0.035 | 0.035 |
| Citric acid anhydrous | | 0.345 | 0.345 |
| Ascorbic acid | 0.3 | 0.3 | 0.3 |
| EDTA | 0.003 | 0.003 | 0.003 |
| Glutathione | | | 0.15 |
| Benzyl alcohol | 0.3 | 0.3 | 0.3 |
| pH | 6.5 | 6.5 | 6.5 |
| WFI qs (mL) | 30 | 30 | 30 |

*Corrected based on water content (85%) of API: 0.03 g/0.85

Preparation Procedure
1. Weigh out components except WFI into a depyrogenated glass bottle based on compounding table.
2. Add about 20 mL WFI, shake to dissolve
3. Adjust pH to 6.5 using 6N HCl/NaOH immediately
4. QS with WFI immediately
5. Aseptically in a biosafety hood, fill 30 mL into each 30-mL sterile glass vial by passing thru a 0.2-micron syringe filter, seal the vials immediately
6. Place upstanding position in the stability chambers Test
7. Record appearance
8. HPLC for assay and impurity
9. pH Stability Results

Appearance

| Sample ID | Temp (° C.) | T = 0 (Initial) | 2 weeks |
|---|---|---|---|
| F44 | 25 | Clear & colorless | Yellow and ppt |
| | 40 | Clear & colorless | Yellow and ppt |
| F46 | 25 | Clear & colorless | Yellow |
| | 40 | Clear & colorless | Yellow |
| F47 | 25 | Clear & colorless | Clear & colorless |
| | 40 | Clear & colorless | Clear & colorless | pH

| Sample ID | Temp (° C.) | T = 0 (Initial) | 2 weeks |
|---|---|---|---|
| F46 | 25 | 6.59 | 6.50 |
| | 40 | | 6.48 |
| F47 | 25 | 6.54 | 6.50 |
| | 40 | | 6.45 |

| Assay (mg/mL) by HPLC | | | |
|---|---|---|---|
| Sample ID | Temp (° C.) | T = 0 (Initial) | 2 weeks |
| F46 | 25 | 1.02 | 1.00 |
|  | 40 |  | 1.00 |
| F47 | 25 | 1.01 | 1.01 |
|  | 40 |  | 1.01 |

| % Assay recovery (over initial) | | | |
|---|---|---|---|
| Sample ID | Temp (° C.) | T = 0 (Initial) | 2 weeks |
| F46 | 25 | 100 | 98.1 |
|  | 40 |  | 97.9 |
| F47 | 25 | 100 | 100.1 |
|  | 40 |  | 100.2 |

| Total chromatographic purity (% Peak Area) | | | |
|---|---|---|---|
| Sample ID | Temp (° C.) | T = 0 (Initial) | 2 weeks |
| F47 | 25 | 99.2 | 97.6 |
|  | 40 | 99.2 | 97.7 |

| Impurity profile of F47 at Day 0 (RT: Retention time) | | | |
|---|---|---|---|
|  | Impurity 1 | | Impurity 2 | |
| Temp (° C.) | RT | % | RT | % |
| 25 | 9.3 | 0.61 | 18.5 | 0.15 |

| Impurity profile F47 at 2 week (RT: Retention time) | | | | | | | | | |
|---|---|---|---|---|---|---|---|---|---|
| | Impurity 1 | | Impurity 2 | | Impurity 3 | | Impurity 4 | | Impurity 5 | |
| Temp (° C.) | RT | % | RT | % | RT | % | RT | % | RT | % |
| 25 | 9.3 | 0.68 | 10.6 | 0.71 | 18.5 | 0.22 | 24.2 | 0.85 | | |
| 40 | 9.3 | 0.62 | 10.4 | 0.21 | 10.6 | 0.33 | 18.4 | 0.22 | 24.2 | 0.86 |

EXAMPLE 6

F48 is a room temperature flavored sublingual drop.

Further, testing has revealed that the above compositions/formulations do not require refrigeration in order to retain their potency.

Although the invention has been described with reference to the above example, it will be understood that modifications and variations are encompassed within the spirit and scope of the invention. Accordingly, the invention is limited only by the following claims.

What is claimed is:

1. A method of preparing a solution containing 5-methyltetrahydrofolate retaining a potency of between about 90 to 110% for at least 1 month when stored between about 2° C. and 8° C., comprising the steps of:
    determining the weight of 5-methyltetrahydrofolate powder and sodium metabisulfite;
    determining the water content of the 5-methyltetrahydrofolate;
    adding an excess of 5-methyltetrahydrofolate powder of between about 5% and 25% of the determined weight of 5-methyltetrahydrofolate powder;
    adding approximately 75% of the total desired volume of sterile water and mixing while keeping the mixture cold;
    mixing an appropriate amount of preservative into the mixture while keeping the mixture cold;
    adding a suitable pH adjuster to adjust the pH to between approximately 3 and 9 while keeping the mixture cold; and
    adding enough sterile water to bring the mixture to the desired volume while protecting the mixture from light and keeping the mixture cold, wherein 5-methyltetrahydrofolate or a mixture containing 5-methyltetrahydrofolate is protected from light.

2. The method of claim 1, wherein the excess of 5-methyltetrahydrofolate powder is about 15% of the determined weight of 5-methyltetrahydrofolate powder.

3. The method of claim 2, wherein the preservative comprises benzyl alcohol.

4. The method of claim 2, wherein the pH adjuster comprises sodium phosphate dibasic solution between about 1% to 20%.

5. The method of claim 4, wherein the preservative comprises benzyl alcohol.

6. The method of claim 1, wherein the preservative comprises benzyl alcohol.

7. The method of claim 6, wherein the preservative comprises benzyl alcohol.

8. The method of claim 6, wherein the pH adjuster comprises sodium phosphate dibasic solution between about 1% to 20%.

9. The method of claim 8, wherein the preservative comprises benzyl alcohol.

10. The method of claim 1, wherein the pH is adjusted to between approximately 4 and 8.

11. The method of claim 10, wherein the pH adjuster comprises sodium phosphate dibasic solution between about 1% to 20%.

12. The method of claim 11, wherein the preservative comprises benzyl alcohol.

13. The method of claim 1, wherein the pH is adjusted to between approximately 5 and 5.7.

14. The method of claim 13, wherein the preservative comprises benzyl alcohol.

15. The method of claim 13, wherein the pH adjuster comprises sodium phosphate dibasic solution between about 1% to 20%.

16. The method of claim 15, wherein the preservative comprises benzyl alcohol.

17. The method of claim 1, wherein the pH adjuster comprises sodium phosphate dibasic solution between about 1% to 20%.

18. The method of claim 17, wherein the preservative comprises benzyl alcohol.

19. The method of claim 1, further comprising adding one or more compounds selected from the group consisting of Methylcobalamin, Hydroxocobalamin, Adenosylcobalamin, Thiamine, Riboflavin-5-phosphate, Niacinamide, Pyridoxine, Dexpanthenol, Biopterin, Inositol, Choline, Methionine and Glutathione.

20. The method of claim 1, further comprising adding Methylcobalamin.

21. The method of claim 1, wherein the solution retains potentcy for at least 6 months.

* * * * *

UNITED STATES PATENT AND TRADEMARK OFFICE
CERTIFICATE OF CORRECTION

| | |
|---|---|
| PATENT NO. | : 10,406,159 B2 |
| APPLICATION NO. | : 15/546650 |
| DATED | : September 10, 2019 |
| INVENTOR(S) | : Hubers et al. |

It is certified that error appears in the above-identified patent and that said Letters Patent is hereby corrected as shown below:

On the Title Page

Column 1 item (72) (inventors), after "Christine A. Givant, Solana Beach, CA (US)" insert -- Andrew X. Chen, San Diego, CA (US); Jianmen Xu, San Diego, CA (US) --.

Signed and Sealed this
Sixth Day of August, 2024

*Katherine Kelly Vidal*

Katherine Kelly Vidal
*Director of the United States Patent and Trademark Office*